US011589851B2

(12) United States Patent
Purohit et al.

(10) Patent No.: US 11,589,851 B2
(45) Date of Patent: Feb. 28, 2023

(54) BIOPSY FORCEPS WITH SERRATED CUTTING JAWS (71) Applicant: Boston Scientific Limited, Galway (IE)

(72) Inventors: Hitendra Purohit, Vadodara (IN); Nishant Randhawa, Chandigarh (IN); Agrim Mishra, New Delhi (IN); Charudatta Chandrakant Aradhye, Solapur (IN); Venkatesh Neelamegam, Tirupur (IN); Nidhi Dhingra, Ludhiana (IN); Dane T. Seddon, Boston, MA (US)

(73) Assignee: Boston Scientific Limited, Galway (IE)

( * ) Notice: Subject to any disclaimer, the term of this patent is extended or adjusted under 35 U.S.C. 154(b) by 149 days.

(21) Appl. No.: 16/355,899

(22) Filed: Mar. 18, 2019

(65) Prior Publication Data
US 2019/0282219 A1    Sep. 19, 2019

Related U.S. Application Data (60) Provisional application No. 62/644,892, filed on Mar. 19, 2018.

(51) Int. Cl.
*A61B 10/06* (2006.01)
*A61B 17/295* (2006.01)
(Continued)

(52) U.S. Cl.
CPC .............. *A61B 10/06* (2013.01); *A61B 10/04* (2013.01); *A61B 17/282* (2013.01); *A61B 17/29* (2013.01);
(Continued)

(58) Field of Classification Search
CPC ..... A61B 10/0266; A61B 10/04; A61B 10/06; A61B 17/282; A61B 17/29; A61B 17/295;
(Continued)

(56) References Cited

U.S. PATENT DOCUMENTS

D71,440 S     11/1926  Villaret
4,682,606 A    7/1987  De Caprio
(Continued)

FOREIGN PATENT DOCUMENTS

EP    2 324 773       5/2011
JP    2006527633 A   12/2006
WO    WO 98/40015    9/1998

OTHER PUBLICATIONS

Engineering ToolBox, (2003). Young's Modulus—Tensile and Yield Strength for common Materials. Version Sep. 18, 2015. [online] Available at: https://www.engineeringtoolbox.com/young-modulus-d_417.html. Accessed via Wayback Machine Feb. 16, 2021. (Year: 2015).*

(Continued)

*Primary Examiner* — Christian Jang
*Assistant Examiner* — Anna Roberts
(74) *Attorney, Agent, or Firm* — Bookoff McAndrews, PLLC (57) ABSTRACT A biopsy forceps device includes a tension member and an end effector including first and second jaws movable between an open configuration, in which the jaws are separated from one another to receive target tissue therebetween, and a closed configuration, in which cutting edges of the jaws are moved toward one another to cut a portion of the target tissue. The jaws define a tissue receiving space therebetween to house the cut tissue. The jaws are pivotable relative to one another, each of the jaws including a serrated cutting edge extending therealong, the end effector further including a tension member attachment including a proximal end coupled to the tension member. The attachment is movably coupled to the jaws so that distal movement of the attachment moves the jaws to the open configuration while (Continued)

proximal movement thereof moves the jaws to the closed configuration.

18 Claims, 7 Drawing Sheets

(51) Int. Cl.
  *A61B 10/04* (2006.01)
  *A61B 17/28* (2006.01)
  *A61B 17/29* (2006.01)
  *A61B 10/02* (2006.01)

(52) U.S. Cl.
  CPC ........ *A61B 17/295* (2013.01); *A61B 10/0266* (2013.01); *A61B 2010/0208* (2013.01); *A61B 2017/2901* (2013.01); *A61B 2017/2926* (2013.01)

(58) Field of Classification Search
  CPC .... A61B 2017/2901; A61B 2017/2926; A61B 2010/0208
  See application file for complete search history.

(56) References Cited

U.S. PATENT DOCUMENTS

| | | | |
|---|---|---|---|
| 5,304,203 A | | 4/1994 | El-Mallawany et al. |
| 5,553,624 A | | 9/1996 | Francese et al. |
| 5,779,646 A | | 7/1998 | Koblish et al. |
| 5,819,738 A | * | 10/1998 | Slater .................... A61B 10/06 600/564 |
| 5,906,630 A | | 5/1999 | Anderhub et al. |
| 6,036,656 A | | 3/2000 | Slater |
| 6,309,404 B1 | | 10/2001 | Krzyzanowski |
| 6,394,964 B1 | | 5/2002 | Sievert et al. |
| 6,514,269 B2 | | 2/2003 | Yamamoto |
| 8,672,859 B2 | | 3/2014 | Timberlake et al. |
| 8,740,853 B2 | | 6/2014 | Szweda et al. |
| 9,592,035 B2 | | 3/2017 | Vetter et al. |
| 9,681,857 B2 | | 6/2017 | Rothberg et al. |
| 2004/0260337 A1 | | 12/2004 | Freed |
| 2006/0184198 A1 | | 8/2006 | Bales et al. |
| 2007/0244509 A1 | | 10/2007 | Weizman et al. |
| 2009/0264795 A1 | * | 10/2009 | Dunn ................. A61B 10/0233 600/567 |
| 2013/0066230 A1 | | 3/2013 | Li et al. |
| 2013/0085412 A1 | * | 4/2013 | Timberlake ............ A61B 10/00 600/564 |
| 2013/0131544 A1 | | 5/2013 | Bowden et al. |
| 2015/0148803 A1 | | 5/2015 | Kaneko et al. |
| 2016/0100851 A1 | | 4/2016 | Van Andel |
| 2016/0256140 A1 | * | 9/2016 | Haack .................... A61B 17/29 |
| 2016/0262735 A1 | | 9/2016 | Gundberg et al. |
| 2017/0071585 A1 | | 3/2017 | Adkisson et al. |
| 2020/0054309 A1 | * | 2/2020 | Krzyzanowski ....... A61B 10/04 |

OTHER PUBLICATIONS

Official Communication in European Patent Application No. 19717609.2, dated Aug. 30, 2022 (5 pages).

Office Action in Japanese Patent Application No. 2020-542143, dated Dec. 6, 2022 (7 pages).

\* cited by examiner

BIOPSY FORCEPS WITH SERRATED CUTTING JAWS

PRIORITY CLAIM

This present disclosure claims priority to U.S. Provisional Patent Application Ser. No. 62/644,892 filed Mar. 19, 2018; the disclosure of which is incorporated herewith by reference.

FIELD OF INVENTION

The present disclosure relates to endoscopic instruments, and more specifically, to biopsy forceps for use in endoscopic procedures.

BACKGROUND

Tissue samples are often examined to determine the presence of a pathological disorder. Endoscopic biopsy forceps may be used in conjunction with an endoscope for taking certain tissue samples from the human body for analysis. Often, the samples must be obtained from deep within the body at locations that are difficult to access using standard forceps jaws (e.g., tissue from areas accessible only via tortuous biliary paths). In certain cases, the quality or amount of tissue easily accessible by a physician using standard forceps may not be sufficient for pathologists to make an accurate diagnosis. Furthermore, forceps jaws are often difficult to maneuver as needed to obtain bites tangential to an axis along which the forceps are inserted to the target area. Thus, improved endoscopic biopsy forceps which can easily navigate tortuous paths while increasing tissue anchoring and increasing depth of tissue penetration are desirable.

SUMMARY

The present disclosure is directed to a biopsy forceps device comprising a tension member extending from a proximal end to a distal end and an end effector including first and second jaws movable between an open configuration, in which the jaws are separated from one another to receive target tissue therebetween, and a closed configuration, in which cutting edges of the jaws are moved toward one another to cut a portion of the target tissue from surrounding tissue, the first and second jaws defining a tissue receiving space therebetween to house the cut tissue, the first and second jaws being pivotable relative to one another, each of the jaws including a serrated cutting edge extending therealong, the end effector further including a tension member attachment extending from a distal end to a proximal end coupled to the tension member, the tension member attachment being movably coupled to the first and second jaws so that distal movement of the tension member attachment moves the jaws to the open configuration while proximal movement thereof moves the jaws to the closed configuration.

In an embodiment, the serrated cutting edges define a plurality of teeth.

In an embodiment, the plurality of teeth include first teeth having a first height and second teeth having a second height different from the first height.

In an embodiment, the first teeth and second teeth are alternate along a length of the first and second jaws.

In an embodiment, the plurality of teeth symmetrically and incrementally decrease in height proximally from distal ends of the first and second jaws.

In an embodiment, the plurality of teeth of the first jaw and the plurality of teeth of the second jaw are offset from one another such that the plurality of teeth of the first and second jaws have a complimentary fit when in the closed configuration.

In an embodiment, the first and second jaws include concave inner surfaces defining a substantially hemispherical cup.

In an embodiment, the first and second jaws each include a hole extending therethrough from an outer surface to the inner surface.

In an embodiment, the first and second jaws are formed from a metal material.

In an embodiment, each of the first and second jaws include a flexible polymeric portion formed of a polymeric material.

The present disclosure is also directed to a biopsy forceps system for sampling tissue comprising a proximal assembly including an actuator, a tension member extending from a distal end to a proximal end coupled to the proximal assembly, and a distal assembly including first and second jaws movable between an open configuration, in which the jaws are separated from one another to receive target tissue therebetween, and a closed configuration, in which cutting edges of the jaws are moved toward one another to cut a portion of the target tissue from surrounding tissue, the first and second jaws defining a tissue receiving space therebetween to house the cut tissue, the first and second jaws being pivotable relative to one another, each of the jaws including a serrated cutting edge extending therealong, the end effector further including a tension member attachment extending from a distal end to a proximal end coupled to the tension member, the tension member attachment being movably coupled to the first and second jaws so that distal movement of the tension member attachment moves the jaws to the open configuration while proximal movement thereof moves the jaws to the closed configuration, wherein actuation of the proximal assembly causes the tension member attachment to move proximally and distally relative to the first and second jaws.

In an embodiment, the serrated cutting edges define a plurality of teeth.

In an embodiment, the plurality of teeth include first teeth having a first height and second teeth having a second height different from the first height.

In an embodiment, the first teeth and second teeth are alternate along a length of the first and second jaws.

In an embodiment, the plurality of teeth symmetrically and incrementally decrease in height proximally from distal ends of the first and second jaws.

The present disclosure is also directed to a method of obtaining a tissue sample comprising inserting a distal portion of a biopsy forceps assembly to a target area within a living body, the distal portion including a tension member extending from a proximal end to a distal end and an end effector including first and second jaws movable between an open configuration, in which the jaws are separated from one another to receive target tissue therebetween, and a closed configuration, in which cutting edges of the jaws are moved toward one another to cut a portion of the target tissue from surrounding tissue, the first and second jaws defining a tissue receiving space therebetween to house the cut tissue, the first and second jaws being pivotable relative to one another, each of the jaws including a serrated cutting edge extending therealong, the end effector further including a tension member attachment extending from a distal end to a proximal end coupled to the tension member, the tension member attachment being movably coupled to the first and second jaws so that distal movement of the tension member attachment moves the jaws to the open configuration while proximal movement thereof moves the jaws to the closed configuration, and moving the tension member proximally relative to the first and second jaws to pivot the jaws to the closed configuration so that cutting edges of the first and second jaws sever the target tissue received therebetween from the surrounding tissue.

In an embodiment, the method further includes inserting the biopsy forceps assembly through the working channel of an endoscope.

In an embodiment, the serrated cutting edges define a plurality of teeth, the plurality of teeth including first teeth having a first height and second teeth having a second height different from the first height.

In an embodiment, the first teeth and second teeth are alternate along a length of the first and second jaws.

In an embodiment, the plurality of teeth symmetrically and incrementally decrease in height proximally from distal ends of the first and second jaws.

BRIEF DESCRIPTION

DETAILED DESCRIPTION

The present disclosure may be further understood with reference to the following description and the appended drawings, wherein like elements are referred to with the same reference numerals. The present disclosure relates to an endoscopic forceps assembly for severing and retaining tissue samples. Exemplary embodiments of the present disclosure describe a forceps assembly that can be advanced through a working channel of an endoscope, including, for example, a SpyScope™, or any other endoscopic device specifically designed and/or sized for use with the forceps assembly, and into a tissue tract. Current embodiments also include a more compact forceps design for increasing the passability and maneuverability of the forceps assembly through tight curvatures within the working channels of the endoscopic devices as well as through a tortuous lumen of a living body. Exemplary embodiments of the biopsy forceps assembly include serrated cutting edges which improve the grip of the device on a target tissue surface without slip, increasing the volume of tissue that will be retracted in a single bit. It should be noted that the terms "proximal" and "distal," as used herein, are intended to refer to toward (proximal) and away from (distal) a user of the device.

Figure 1:
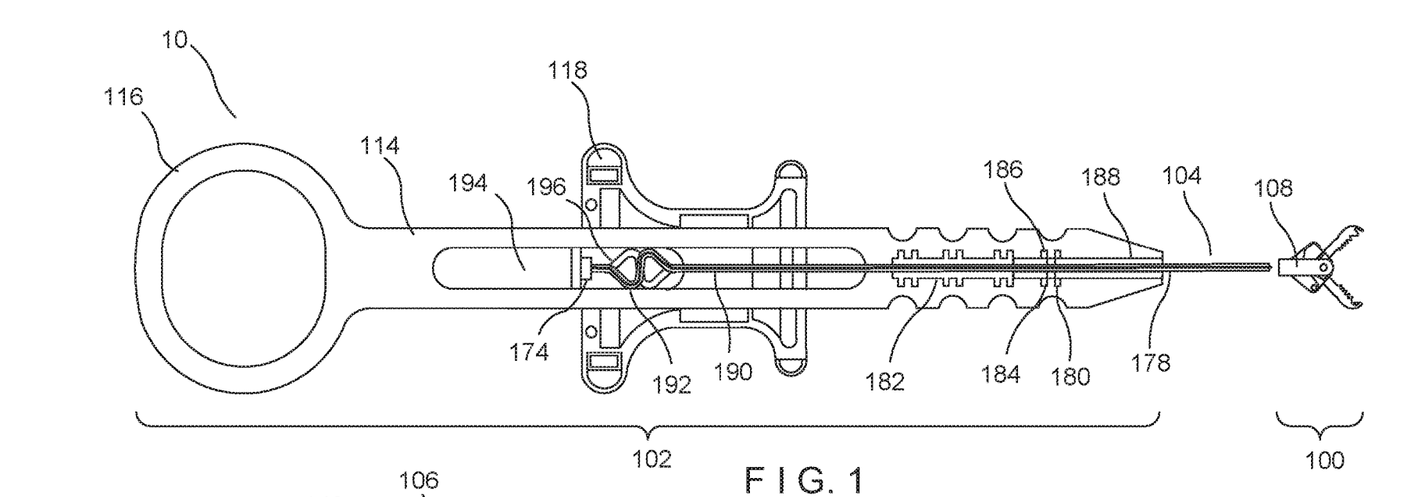
FIG. 1 shows a perspective, partial cross-sectional view of a forceps assembly according to an exemplary embodiment of the present disclosure.
Figure 2:
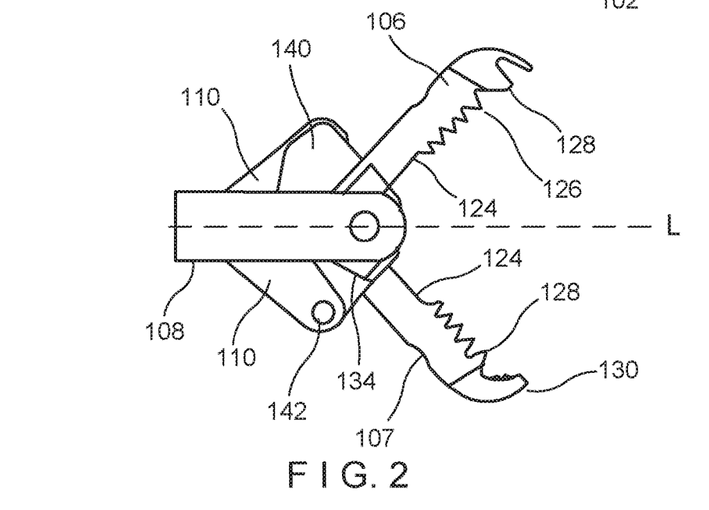
FIG. 2 shows a side view of a distal end effector assembly of the forceps assembly of FIG. 1 according to an exemplary embodiment of the present disclosure.

A forceps assembly 10, according to an exemplary embodiment of the present invention, is depicted in FIG. 1. The forceps assembly 10 includes a distal assembly 100, a proximal assembly 102, and an elongate member 104 connecting the distal assembly 100 to the proximal assembly 102. The distal assembly 100, as shown in FIG. 2, includes a pair of jaws 106, 107, a clevis 108, a pair of links 110 and a control wire attachment 112. The proximal assembly 102, as shown in FIG. 1, includes a handle 114 including a proximal thumb ring 116, and a spool 118 that slides relative to the handle 114. The elongate member 104, in the present embodiment, is a coiled member and houses a tension member such as a control wire 120 that extends from the proximal assembly 102 to the distal assembly 100.

FIGS. 2-6 depict the distal assembly 100 with a first jaw 106 and a second jaw 107 in an open, tissue-receiving configuration. The first and second jaws 106, 107 of this embodiment are generally cup-shaped with convex outer surfaces and concave inner surfaces that, in the closed configuration, define an inner tissue-receiving space 122 between the jaws 106, 107. The outer perimeter edges of the first and second jaws 106, 107 are formed as tissue cutting edges 124 configured to mate with one another when in the closed configuration. The cutting edges 124, in this embodiment, include serrations 126 along their length. For example, each of the cutting edges 124 includes serrations 126 with teeth 128 which symmetrically and incrementally decrease in size proximally from distal ends 130 of the first and second jaws 106, 107, as shown in FIGS. 2-5. The teeth 128 of the first and second jaws 106, 107 are complimentary such that peaks of the teeth of the first jaw 106 fit within the valleys of the serrations of the second jaw 107, and vice versa. This offset fit of the teeth gives the first and second jaws 106, 107 a clean cut on the biopsy tissue without damaging either the tissue or the first and second jaws 106. Each of the first and second jaws 106, 107 includes a hole 132 extending through the center of the jaw from the outer surface to the inner surface. The hole 132 allows for fluids to flow out of the first and second jaws 106, 107, respectively, during tissue retrieval, aiding in increasing a volume of tissue acquired between the first and second jaws 106, 107. The hole 132 further prevents pressure from building in the tissue receiving space 122, avoiding trauma to the captured tissue. The first jaw 106 includes a tang 134 with a pivot hole 136 sized and shaped to receive a pivot pin 138 therethrough. The second jaw 107 also includes a tang 140 defining a similarly sized pivot hole 136 for receiving the pivot pin 138 therethrough. The pivot pin 138 is configured to extend through the pivot holes 136 transverse to a central longitudinal axis, L, of the forceps assembly 10. The first and second jaws 106, 107, respectively, further include actuating pins 142, 144, respectively, extending from an outer surface of the tangs 134, 140 and sized and shaped to be received within corresponding holes 162 on the links 110, as will be discussed in further detail below. The actuating pins 142, 144 are located proximally of the pivot holes 136 with the actuating pin 142 located close to an end of the tang 134 on a side of the axis L opposite the first jaw 106 while the actuating pin 144 is located close to an end of the tang 140 on a side of the axis L opposite the second jaw 107 so that, as the control wire attachment 112 is moved distally, the tangs 134, 140 pivot relative to the links 110 about the actuating pins 142, 144 so that an angle between each of the jaws 106, 107 and its corresponding link 110 decreases from approximately 180 degrees, as shown in FIG. 8, to approximately 90 degrees, as shown in FIG. 7. This motion pivots the first and second jaws 106, 107 away from one another in opposite directions so that the first and jaws 106, 107 move from the closed to the open position.

The clevis 108 is substantially U-shaped and includes a central lumen 150. The clevis 108 includes a pair of arms 152 extending distally from a generally cylindrical proximal portion 154. The central lumen 150 passes through the proximal portion 154 and is sized and shaped to receive the control wire attachment 112 therein. Each arm 152 has a generally curved outer surface and a generally flat inner surface and includes a pivot pin hole 156 to receive the pivot pin 138 therein. A jaw receiving space 158 is defined between the two arms 152 to receive the tangs 134, 140 of the first and second jaws 106, 107, respectively. The pivot pin 138 extends through the pivot pin holes 156 of the arms 152 as well as the pivot holes 136 of the tangs 134, 140 to connect the clevis 108 to the first and second jaws 106, 107 and permit pivotal movement of the first and second jaws 106, 107 relative to one another and the clevis 108. The control wire attachment 112 extends through the central lumen 150 and connects to a distal end of the control wire 120 housed within the elongate member 104. These connections couple the distal assembly 100 to the proximal assembly 102 while the control wire 120 and control wire attachment 112 are used to actuate the jaws 106, 107, as described in further detail below.

Figure 6:
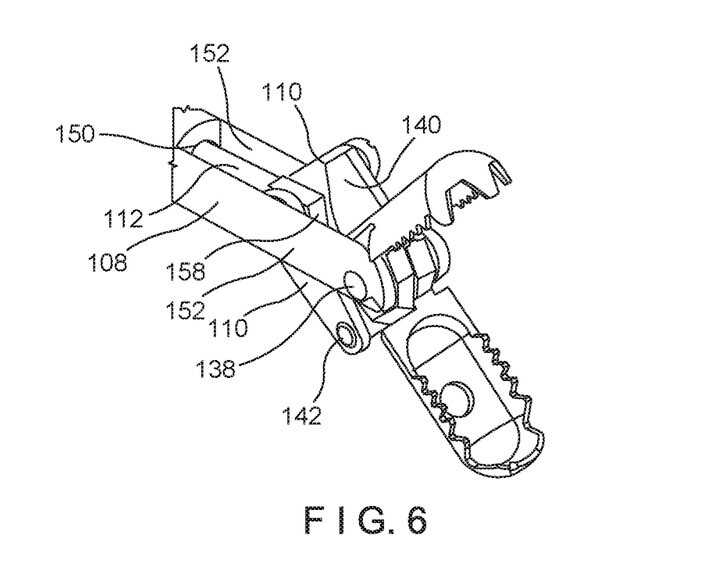
FIG. 6 shows a perspective view of the distal end effector assembly of the forceps assembly of FIG. 1.
Figure 7:
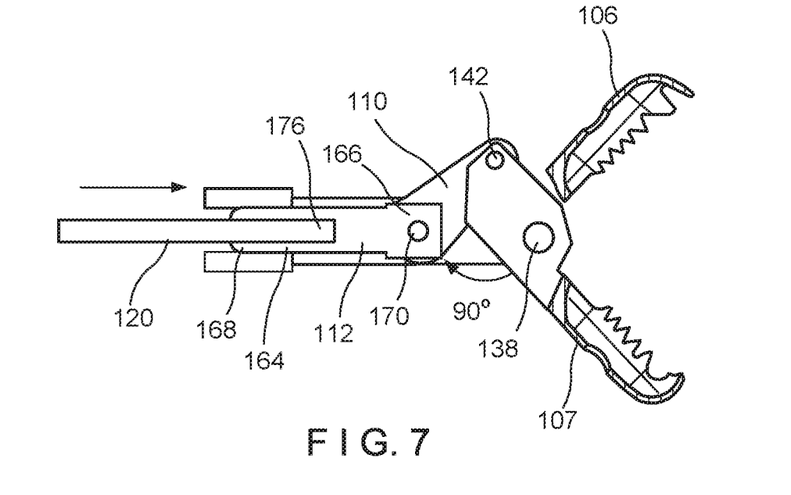
FIG. 7 shows a side view of the distal end effector assembly of the forceps assembly of FIG. 1.
Figure 8:
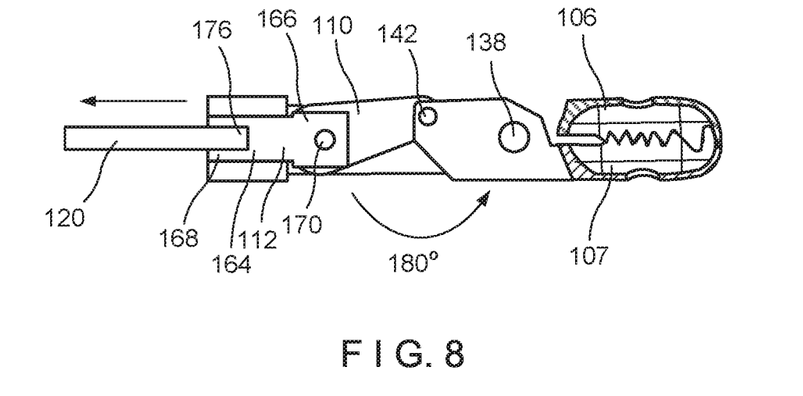
FIG. 8 shows another side view of the distal end effector assembly of FIG. 7.

As noted above, the distal assembly 100 includes a pair of links 110, as seen in FIGS. 6-7. Each link 110 includes a through hole at each of the proximal and distal ends of the link 110. The distal through hole 160 of each link 110 receives the actuating pin 142, 144 of the corresponding one of the first and second jaws 106, 107. Link pins 170 on the control wire attachment 112 extend through the proximal through hole 162 of each link 110 from the distal end of the control wire attachment 112, connecting the links 110 to the control wire attachment 112, as discussed in further detail below. Specifically, a link 110 is positioned on either lateral side of the control wire attachment 112 and coupled to a corresponding one of the first and second jaws 106, 107.

The control wire attachment 112, as shown in FIG. 7, extends from a proximal end to a distal end and includes a proximal part 164 and a distal part 166. The proximal part 164 is substantially cylindrical and defines a central blind hole 168 open at the proximal end. The blind hole 168 is configured to be coupled (e.g., via welding) to the distal end of the control wire 120. The distal part 166 includes generally flat lateral surfaces, each lateral surface including a link pin 170 extending laterally therefrom. Each of the link pins 170 is sized and shaped to fit within a corresponding one of the proximal holes 162 extending through a proximal portion of a corresponding one of the links 110, pivotally coupling the control wire attachment 112 to each of the links 110 and allowing for radial movement of the first and second jaws 106, 107 about a pivot point as the control wire attachment 112 is moved along the longitudinal axis, L, of the forceps assembly 10. Specifically, as the control wire attachment 112 is moved distally, distal ends of the links 110 are moved distally and forced to pivot radially away from the longitudinal axis of the distal assembly 100, forcing the first and second jaws 106, 107 to pivot relative to the links 110 in opposite directions opening the first and second jaws 106, 107. Conversely, as the control wire attachment 112 is moved proximally, the links 110 are pulled proximally such that the links 110 and the first and second jaws 106, 107 pivot about their respective pins, moving the distal ends of the links 110 and the proximal ends of the jaws 106, 107 toward the longitudinal axis L of the device to move the first and second jaws 106, 107 toward one another into the closed configuration.

In an exemplary embodiment, the distal assembly 100 has a rigid portion with a reduced length of, for example, 5.8 mm, when compared to standard forceps end effectors. In another exemplary embodiment, the jaw lengths may be reduced to a rigid length of, for example, 5.8 mm. Furthermore, the clevis 108 is reduced in length by 1.2 mm to a rigid length of, for example, 3.2 mm. The shortening of these components and, thus, the distal assembly 100, allows the distal assembly 100 to more easily pass through acute curvatures within a living body.

Turning back to FIG. 1, the elongate member 104 is coupled to, and extends proximally from, the clevis 108. The elongate member 104 and clevis 108 may be coupled to one another via any of a variety of methods including, but not limited to, welding, soldering, adhesives, etc. In an exemplary embodiment, the elongate member 104 may be formed of a flexible, closely wound, stainless steel helical coil and may further include a thin covering or coating, such as a layer of polytetrafluoroethylene (PTFE) as would be understood by those skilled in the art. As one skilled in the art would understand, other shapes for the cross-section may be selected depending on the particular application. The PTFE reduces friction between the working channel of the endoscope and the elongate member 104 so that the forceps assembly 10 slides more easily within the endoscope.

Figure 3:
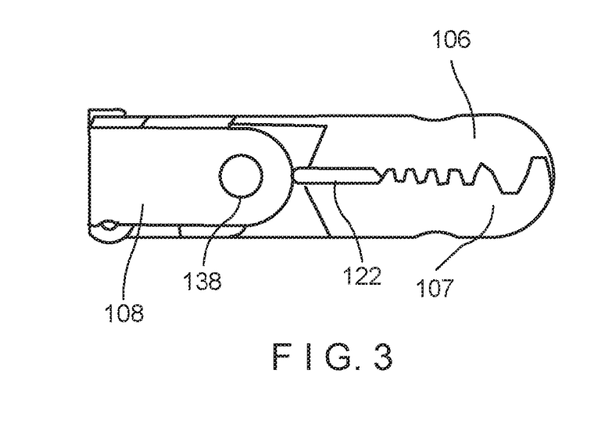
FIG. 3 shows another side view of the distal end effector assembly of FIG. 2 in the closed configuration.
Figure 4:
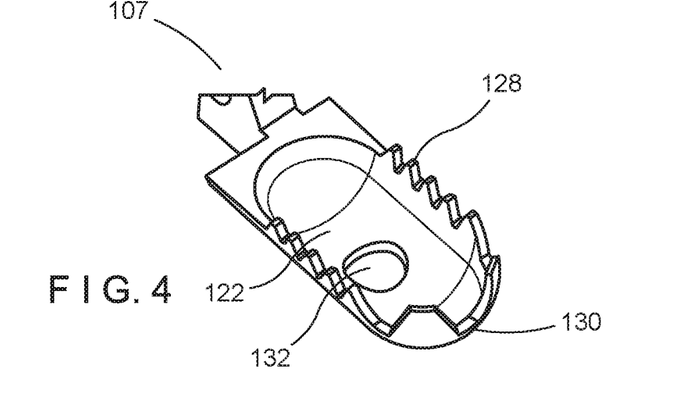
FIG. 4 shows a perspective view of a jaw of the forceps assembly of FIG. 1 according to an exemplary embodiment of the present disclosure.
Figure 5:
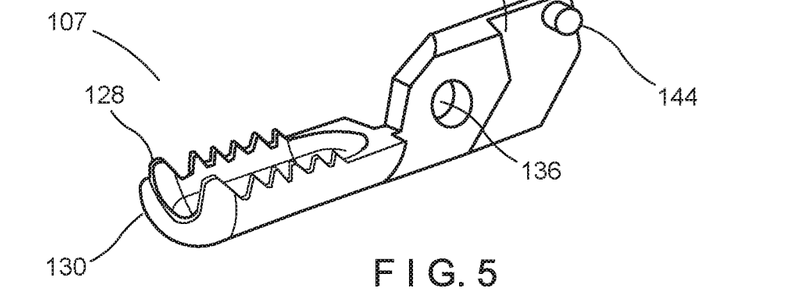
FIG. 5 shows another perspective view of a jaw of the forceps assembly of FIG. 1.

The control wire 120, as depicted in FIG. 1, extends from a proximal end 174 to a distal end 176 (shown in FIG. 8) and is sized and shaped to be slidably movable within the elongate member 104. The proximal end 174 of the control wire 176 is inserted into a hypotube 190 and connected to the spool 118 which is movable along the longitudinal axis of the forceps assembly 10 for actuation of the control wire 120. At the distal end 176, the control wire 120 is coupled to the proximal end of the control wire attachment 112, as can be seen in FIG. 3. The control wire 120 and the control wire attachment 112 may be coupled via any suitable means such as, for example, welding, soldering, adhesives, etc. In an exemplary embodiment, the control wire 120 is sufficiently flexible to be passed through a working channel of an endoscope inserted to a target site within the body via, for example, a natural body lumen accessed via a bodily orifice and passed along the body lumen along a tortuous path. The control wire 120 is preferably formed of a material such as stainless steel exhibiting a torsional stiffness sufficient to transmit rotational force to the distal end of thereof. The control wire 120 may have a constant diameter along its length or may vary depending on the application. For example, in one embodiment, the control wire 120 may include a taper towards its distal end to facilitate insertion into the control wire attachment 112. In an embodiment, the control wire 120 may including a PTFE coating to reduce friction between the control wire 120 and the elongate member 104.

FIG. 1 depicts the proximal assembly 102 of the forceps assembly 10, including the handle 114, with the thumb ring 116, and spool 118. As seen in FIG. 1, the elongate member 104 of this embodiment includes a coil 178 and a coil retainer 180. The elongate member 104 extends proximally from the clevis 108 to connect to the handle 114. To facilitate a wide range of applications and reach targeted anatomical regions of small cross-section, the elongated biopsy forceps assembly 10 may be formed to have a length of between 270 cm and 300 cm, and more preferably between 270 cm and 290 cm. The spool 118 is movable along the longitudinal axis of the forceps assembly 10 and is sized and shaped to be grasped by the user. As noted above, the movable control wire 120 connects to a proximal end of tang 140 of the control wire attachment 112, depicted in FIG. 1, and extends proximally within, and is configured to slide relative to, the elongate member 104. The proximal end 174 of the control wire 120 couples to the movable spool 118 to permit the user to actuate the forceps assembly 10.

The handle 114 is hollow and defines a lumen 182 which houses the coil retainer 180. Dual fixation flanges 184 on the coil retainer 180 prevent longitudinal movement of the coil retainer 180 within the handle 114. Specifically, the flanges 184 mate with corresponding coil retainer flanges 186 formed within the handle 114 perpendicular to the longitudinal axis of the lumen 182. A proximal end 188 of the coil 178 is coupled (e.g., welded) to the coil retainer 180 with a proximal-most face of the coil 178 abutting a distal face of the coil retainer 180. In another embodiment, the coil retainer 180 is formed integrally with the coil 178. As noted above, the coil retainer flanges 186 prevent the coil retainer 180 from moving longitudinally within the lumen 182 of the handle 114.

Still referring to FIG. 1, the coil retainer 180 houses a hypotube 190 configured to slide within the coil retainer 180. The hypotube 190 is configured to receive the proximal end of the control wire 120 therein. The control wire 120 is secured by a friction fit within an "S" bend 192 at a proximal end of the hypotube 190 and is prevented from movement relative to the hypotube 190. Alternatively, the control wire 120 may be secured to fit within the "S" bend 192 simply be means of the curved geometry of the hypotube 190. Regardless, this fit, either frictional or geometric, provides sufficient coupling of the control wire 120 to the hypotube 190 such that no other means or method of fixation is necessary to transfer movement of the hypotube 190 to the control wire 120. The handle 114 includes an oval-shaped slot 194 that receives the hypotube 190 housing the proximal end of the control wire 120. The movable spool 118 includes an interior surface that slides along the outside of the handle 114 and slot 194. The spool 118 also includes an integral portion received within the slot 194 which has an "S" channel 196 configured to receive the combined hypotube 190 and control wire 120. As noted above with respect to the control wire 120, the fit may be secured simply by means of geometry of the channel 196. Thus, movement of the spool 118 relative to the handle 114 moves the control wire 120 within the coil 178 permit actuation of the distal assembly 100.

The clevis 108, links 110, control wire attachment 112 and first and second jaws 106, 107 maybe formed of, for example, stainless steel. Alternatively, these components may be formed from aluminum, brass, polymeric materials, nitinol, titanium, or any other suitable biocompatible material. The components may be manufactured through various methods such as, for example, injection molding, precision machining, casting, etc. Other components including the control wire 120, and the pins, also can be manufactured from stainless steel or any other suitable biocompatible material, such as those described above.

Figure 9:
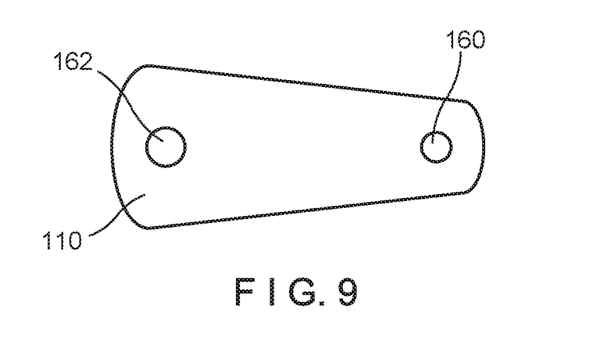
FIG. 9 shows a perspective view of a link of the forceps assembly of FIG. 1.
Figure 10:
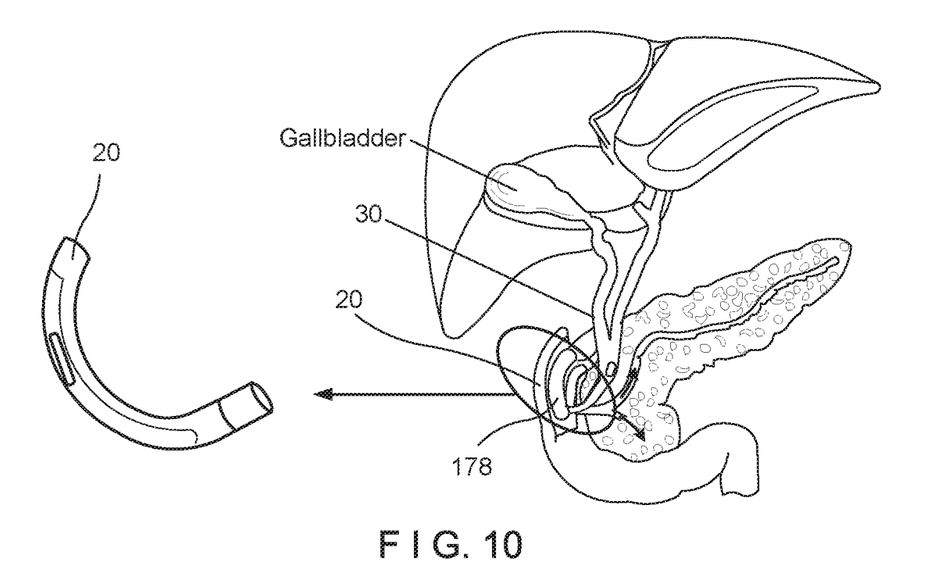
FIG. 10 shows a perspective view of a method of use of the forceps assembly of FIG. 1.

In use, as depicted in FIGS. 9-12, the forceps assembly 10 is maintained in the closed configuration and inserted into the body, e.g., through the working channel of an insertion instrument such as the endoscope 20 which may be, for example, a SpyScope DS™. The PTFE coating of the flexible coil 178 allows the coil 178 to be inserted through the endoscope and into the body with minimal friction while the smaller dimensions of the distal assembly 100 makes delivery through tightly curved tortuous passageways easier because the length of the stiff components of the device (i.e., jaws 106, 107, clevis 108, links 110, control wire attachment 112) is reduced in comparison to traditional biopsy forceps. Specifically, in this embodiment, when a SpyScope™ is inserted into the biliary tract, it forms an acute angle due to the complex anatomy and location of the biliary tract. The reduced rigid length of the distal assembly facilitates passage of the assembly 10 through these tight curves, enhancing maneuverability and positioning at a desired location. Furthermore, as will be discussed in further detail below, the forceps jaws 106, 107 may include polymeric portions which enhance passability of the device through an endoscopic working channel. The coil 178 along with the distal assembly 100 is passed along the tortuous path and, in this exemplary application, positioned in the common bile duct (CBD) 30, as seen in FIG. 9.

Figure 11:
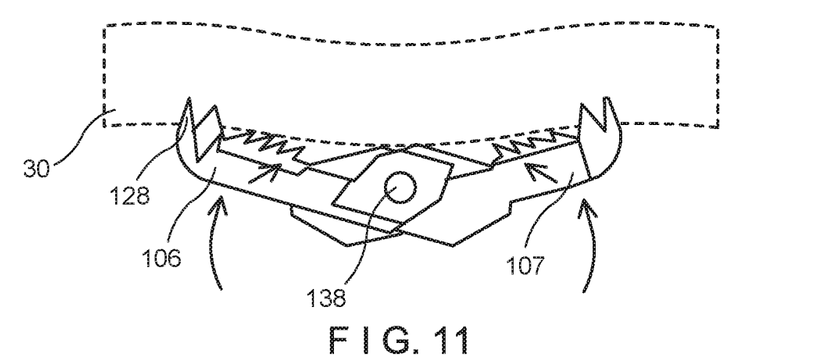
FIG. 11 shows a perspective view of a method of use of the forceps assembly of FIG. 1.
Figure 12:
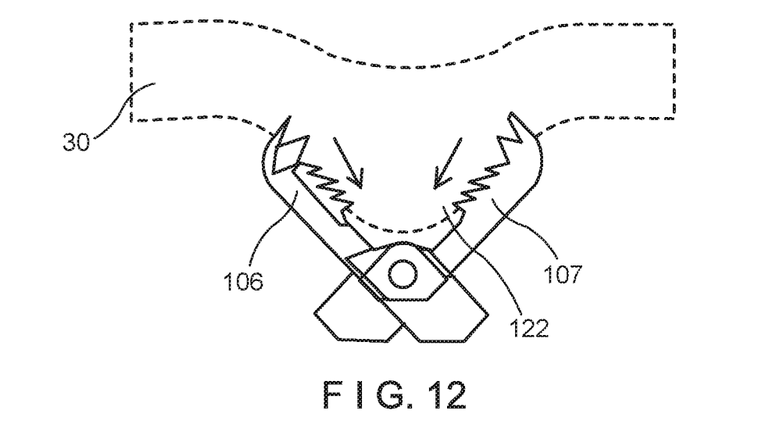
FIG. 12 shows a perspective view of a method of use of the forceps assembly of FIG. 1.
Figure 13:
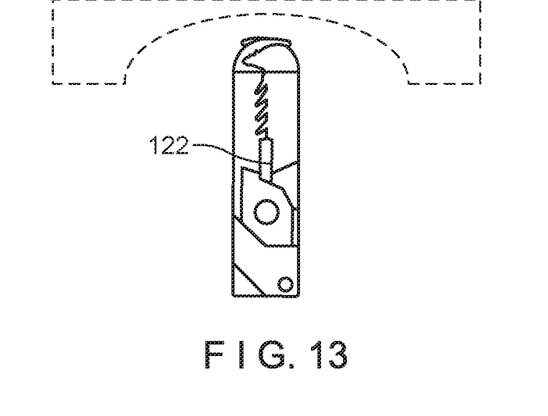
FIG. 13 shows a perspective view of a method of use of the forceps assembly of FIG. 1.

Once the distal assembly 100 has been positioned as desired adjacent to the target tissue, the spool 118 is advanced distally, moving the control wire 120 and thus, the control wire attachment 112 distally. This distal movement of the control wire attachment 112 pivots the links 110 about the link pins 170 and actuating pins 142, 144, pivoting the first and second jaws 106, 107 about the pivot pins 138 to the open, tissue receiving configuration, as shown in FIG. 8. When the first and second jaws 106, 107 open, the first and second jaws 106, 107 are pushed against the common bile duct 30 or other target tissue and the spool 118 is actuated in the opposite direction so the teeth 128 pierce and anchor within the target tissue, helping to increase a depth from which a sample of target tissue may be obtained, as seen in FIG. 11. The first and second jaws 106, 107 are then closed by further withdrawing the spool 118 proximally to withdraw the control wire 120 proximally, pivoting the links 110 about the actuating pins 142, 144 to close the first and second jaws 106, 107, as depicted in FIGS. 11-12. As the first and second jaws 106, 107 close, the control wire attachment 112 pulls the anchored tissue into the first and second jaws 106, 107. At the same time, the cutting edges along the profiles of the first and second jaws 106, 107 sever the tissue captured in the tissue receiving space 109 of the first and second jaws 106, 107 from the surrounding tissue, as shown in FIGS. 11-13. Once the tissue has been collected within the first and second jaws 106, 107, the forceps assembly 10 is retracted proximally from the endoscope and the tissue may be retrieved from the first and second jaws 106, 107 for diagnosis. If more tissue is preferred for the diagnosis, the forceps assembly 10 may be re-inserted through the endoscope for further tissue extraction in the same manner.

Figure 14:
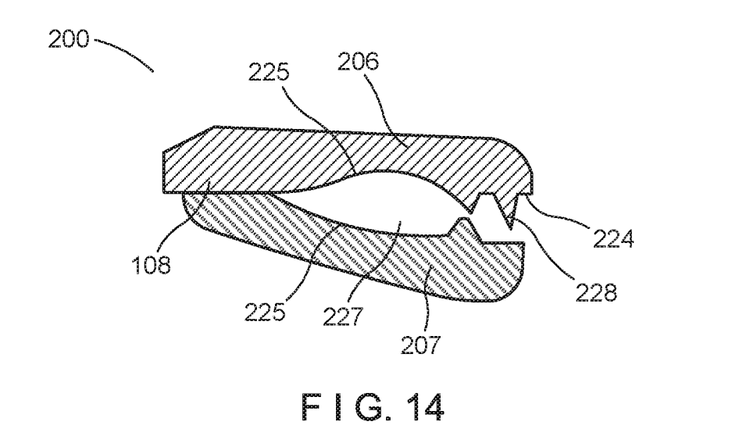
FIG. 14 shows a side view of jaws of the forceps assembly of FIG. 1 according to another exemplary embodiment of the present disclosure.
Figure 15:
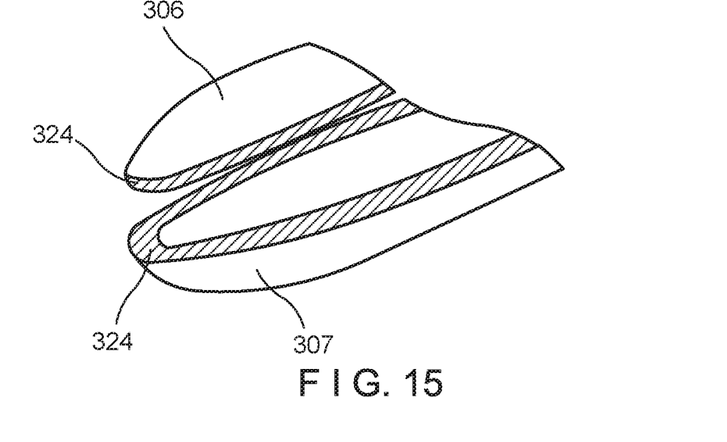
FIG. 15 shows a side view of a jaws of the forceps assembly of FIG. 1 according to a third exemplary embodiment of the present disclosure.
Figure 16:
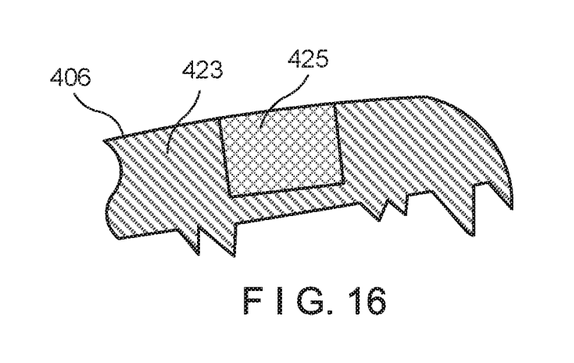
FIG. 16 shows a side view of a jaw of the forceps assembly of FIG. 1 according to a fourth exemplary embodiment of the present disclosure.

FIGS. 14-16 depict particular jaw designs according to further embodiments of the invention. The jaws shown in FIGS. 14-16 are substantially the same as jaws 106, 107 depicted in FIGS. 1-13, except as discussed herein. Regarding FIG. 14, a distal assembly 200 is depicted with a first jaw 206 and a second jaw 207. The jaws 206, 207 of this embodiment are generally cup-shaped with convex outer surfaces and concave inner surfaces. Similar to cutting edges 124, the cutting edges 224 of this embodiment include teeth 228 to facilitate a clean cut of the biopsy tissue. However, in this embodiment, the jaws 206, 207 are configured for a tangential tissue bite with a skiving profile and aggressive teeth. Specifically, as seen FIG. 14, the lateral cutting edges 225 of the jaws 206, 207 are configured as skiving knife edges which allow for cutting of tissue received laterally into the jaws 206, 207, or from a direction perpendicular to the longitudinal axis, L, of the distal assembly 100. The lateral cutting edges 225, in this embodiment, are curved to form windows 227 on opposing sides of the jaws 206, 207, which allow for more tissue to enter into the jaws 206, 207 from the tangential direction. The jaws 206, 207 of this embodiment also include aggressive teeth 228 at a distal portion thereof. That is, some of the teeth 228 may be sharper and may be greater in length than the teeth 128 of jaws 106, 107. The teeth 228 of the jaw 206 are offset from the teeth of the jaw 207 with complimentary profiles so that the jaws 206, 207 are capable of fully closing onto the tissue, improving grip on the tissue.

A pair of jaws 306, 307, according to another exemplary embodiment, is depicted in FIG. 15. Rather than being primarily formed from metal, however, these jaws 306, 307 are formed from a polymer such as, for example, silicone or other elastomers, or may be formed from other medical grade plastic materials. This polymeric material provides the jaws 306, 307 with flexibility for easier maneuverability through a working channel of the endoscope 20 that has been inserted through a tortuous body lumen. To facilitate a clean cut of target tissue received within the jaws 306, 307, metal cutting edges 324 are provided about the perimeter of the jaws 306, 307. Although the FIG. 15 does not show serrations or teeth at the cutting edges 324, it will be understood that serrations of any size and shape may be provided therealong to improve grip on the target tissue.

Another exemplary embodiment of a jaw 406 of that may be paired, as in earlier embodiments, with a similar but oppositely oriented jaw is shown in FIG. 16. In this embodiment, the jaws 406 similar to the jaws 306, 307, is composed of a combination of polymeric and metallic materials. In this embodiment, however, the jaw 406 is formed with a metal portion 423 and a polymeric portion 425. Specifically, the jaw 406 is formed primarily of metal with a portion of the jaw 406 being formed of a polymer to improve flexibility thereof. As seen in FIG. 16, a medial portion of the jaw 406 may be, for example, cut away by laser cutting and then the cut portion 425 is replaced with the polymeric material. In another embodiment, elastomers may be overmolded on to a cut away portion of the jaw 406. While the present embodiment depicts only the jaw 406 with a polymeric portion 425, it will be understood that either one of the jaws or both may include a polymeric portion. Furthermore, the jaws are not limited to a single polymeric portion. Rather, any number of polymeric portions may be included on the jaws, which may be positioned at any part of the jaws so long as the polymeric portions provide a preferred flexibility to the jaws. As shown in the FIG. 16, the jaw 406 of this embodiment includes serrations or teeth. The serrations/teeth may be positioned at any portion of the jaws or may extend around the entire perimeter of the cutting edges.

Figure 17:
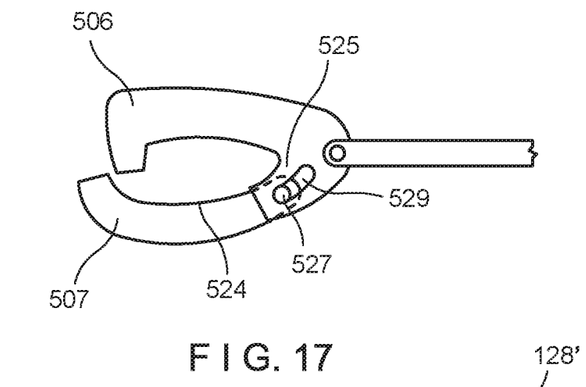
FIG. 17 shows a side view of jaws of the forceps assembly of FIG. 1 according to a fifth exemplary embodiment of the present disclosure.
Figure 18:
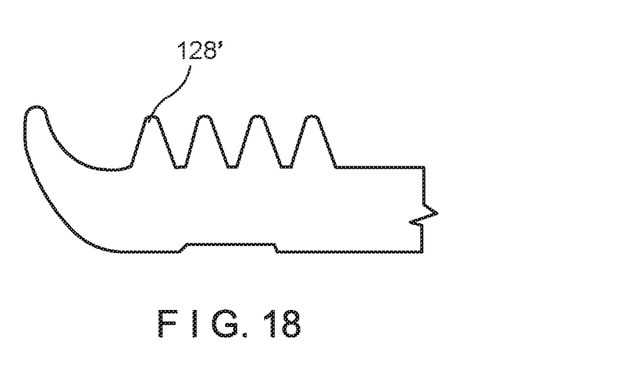
FIG. 18 shows a side view of a jaw of the forceps assembly of FIG. 1 with serrations according to a first exemplary embodiment of the present disclosure.

In another exemplary embodiment shown in FIG. 17, a pair of jaws 506, 507 includes a cam mechanism 525. In this embodiment, the jaw 507 is a fixed jaw that remains stationary when placed around a target tissue. The distal end of the jaw 507 includes a cam pin 527 which slides within a cam slot 529 provided on the jaw 506, as depicted in FIG. 17. Specifically, the cam pin 527 slides in the cam slot 529 such that when the jaw 506 is pulled by the wire, the jaw 506 moves away from jaw 507, opening the jaws 506, 507 to a tissue-capturing position. During opening and closing, the stationary jaw 507 remains in a fixed position, providing the physician with easier positioning of the jaw 506 relative to the target tissue. For example, the physician is able to place the stationary jaw 507 at the target site and close jaw 506 to complete the bite. This functionality prevents slippage of the jaws from the target site and in turn will capture more tissue. Similarly, the jaws 506, 507 are close by moving the wire in a distal direction. Jaws 506, 507 include fenestration hole 524. In an exemplary embodiment, the fenestration hole 524—may be enlarged, allowing for a larger bite by the jaws 506, 507. In an exemplary embodiment, the jaw 506 has a length shorter than that of the jaw 507 so that a distal end of the jaw 506, when in the closed configuration, enters into the jaw 507, creating an interference fit. This cam mechanism 525 of the jaws 506, 507 provides the distal assembly 100 with a bigger bite to obtain a larger volume of tissue, as well as greater maneuverability. Although FIG. 16 does not show serrations or teeth at the cutting edges of fenestration hole 524, it will be understood that serrations of any size and shape may be provided therealong to improve grip on the target tissue.

Figure 19:
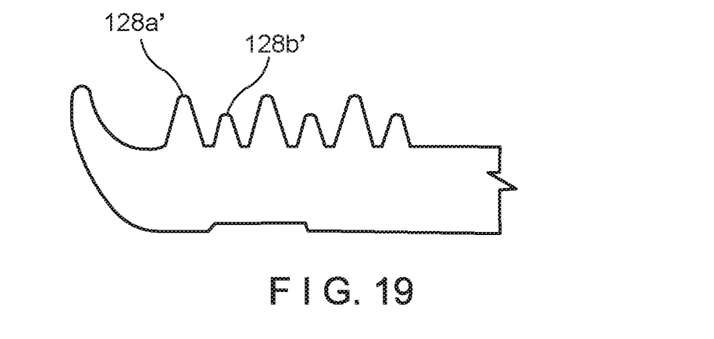
FIG. 19 shows a side view of a jaw of the forceps assembly of FIG. 1 with serrations according to a second exemplary embodiment of the present disclosure.
Figure 20:
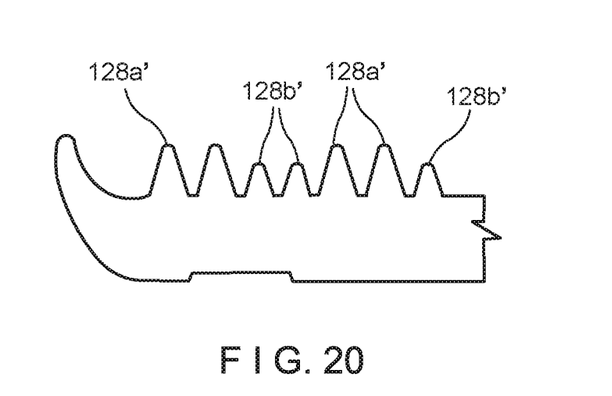
FIG. 20 shows a side view of a jaw of the forceps assembly of FIG. 1 with serrations according to a third exemplary embodiment of the present disclosure.
Figure 21:
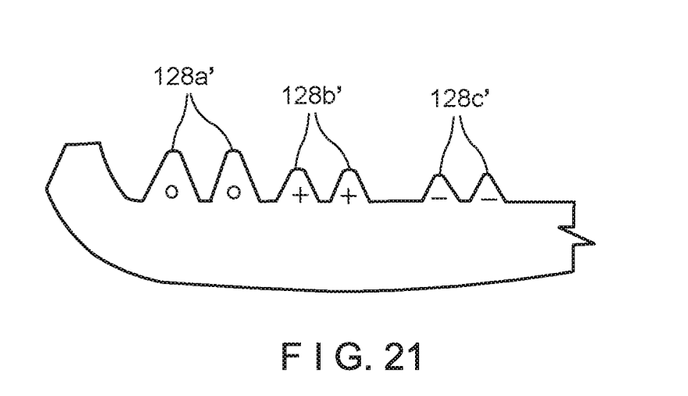
FIG. 21 shows a side view of a jaw of the forceps assembly of FIG. 1 with serrations according to a fourth exemplary embodiment of the present disclosure.
Figure 22:
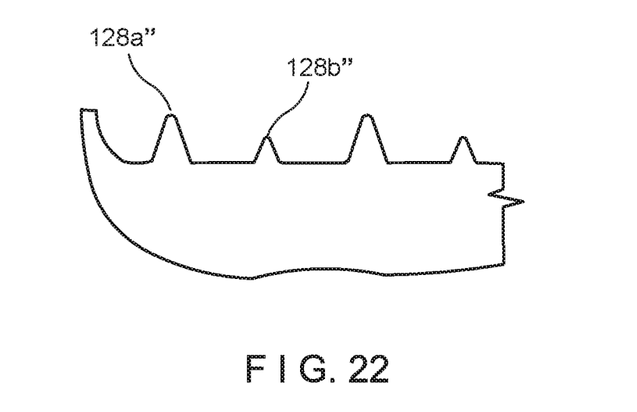
FIG. 22 shows a side view of a jaw of the forceps assembly of FIG. 1 with serrations according to a fifth exemplary embodiment of the present disclosure.

It will be appreciated by those skilled in the art that the serrations or teeth provided on the cutting edges of any of the jaws of any of the previous embodiments may have any of a variety of profiles, sizes and shapes, as will be further described below with reference to FIGS. 18-21. For example, in a first embodiment of FIG. 18, all teeth 128' provided on a jaw may have a uniform height along the length of the cutting edges. In other embodiments, however, the teeth may vary in height. In some embodiments, teeth of different heights may alternate along the length of the cutting edges. For example, FIG. 19 depicts a cutting jaw provided with short teeth 128b' of a first height and long teeth 128a' of a second height which are alternatingly positioned about the cutting edge. Alternatively, FIG. 20 depicts a plurality of short teeth 128b' and long teeth 128a' alternating in increments of two. It will be understood that teeth of different heights may alternate in increments of any number depending on the procedure and application in which the forceps are being used. FIG. 21 depicts a jaw that has progressive pairs of teeth 128a', 128b', 128c' positioned in descending height from a distal end of the jaw to a proximal end of the jaw. In some embodiments, the teeth may have similar heights but vary in pitch. In other 10 embodiments, both pitch and height vary for each tooth. As depicted in FIG. 22, teeth may vary in pitch as well as height along the length of the jaw cutting edge. For example, teeth 128a'' have a greater pitch and height than that of 128b''. Variation in terms of teeth profiles and pitch will lead to better outcomes of tissue size and bite quality. For example, the jaws of FIGS. 18-21 which include a combination of bigger and smaller teeth will have better anchoring on tissue due to bigger teeth while the jaws of FIG. 22 will result in better tangential bites.

It will be appreciated by those skilled in the art that changes may be made to the embodiments described above without departing from the inventive concept thereof. It should further be appreciated that structural features and methods associated with one of the embodiments can be incorporated into other embodiments. It is understood, therefore, that this invention is not limited to the particular embodiment disclosed, but rather modifications are also covered within the scope of the present invention as defined by the appended claims.

What is claimed is:

1. A biopsy forceps device, comprising:
    a tension member extending from a proximal end to a distal end; and
    an end effector including a first jaw and a second jaw movable between an open configuration, in which the first jaw and the second jaw are separated from one another to receive target tissue therebetween, and a closed configuration, in which cutting edges of the first jaw and the second jaw are moved toward one another to cut a portion of the target tissue from surrounding tissue, the first jaw and the second jaw defining a tissue receiving space between a base of the first jaw and an opposing base of the second jaw to house the cut tissue, the first jaw and the second jaw being pivotable relative to one another, each of the first jaw and the second jaw including a serrated cutting edge extending therealong, the serrated cutting edge of the first jaw including a plurality of first teeth, the plurality of first teeth comprising all of the teeth on the serrated cutting edge of the first jaw, and the serrated cutting edge of the second jaw including a plurality of second teeth, the end effector further including an attachment member extending from a distal end to a proximal end directly coupled to the tension member, the attachment member being movably coupled to the first and second jaws so that distal movement of the attachment member moves the jaws to the open configuration while proximal movement thereof moves the jaws to the closed configuration, wherein each of the first jaw and the second jaw extends from a distal end to a proximal end, and wherein a plurality of valleys between the plurality of first teeth define a first line, and wherein the first line intersects each of the plurality of valleys between the plurality of first teeth at a maximum depth of each of the plurality of valleys, at least two peaks of the plurality of first teeth on a first side of the first jaw define a second line parallel to the first line, and at least two more peaks of the plurality of first teeth on the first side of the first jaw define a third line different from the second line and parallel to the first line and the second line.

2. The device of claim 1, wherein the first and second jaws are formed from a metal material, and wherein each of the first and second jaws includes a flexible polymeric portion formed of a polymeric material.

3. The device of claim 1, wherein each of at least some of the plurality of first teeth of the first jaw and each of at least some of the plurality of second teeth of the second jaw comprises a first cutting edge and a second cutting edge such that the respective tooth has a triangular shape.

4. The device of claim 1, wherein each of at least one of the plurality of first teeth of the first jaw and at least one of the plurality of second teeth of the second jaw comprises a first cutting edge, a second cutting edge, and a third cutting edge separating the first cutting edge and the second cutting edge such that the respective tooth has a trapezoidal shape.

5. The device of claim 1, wherein each tooth of the plurality of first teeth of the first jaw is configured as a skiving knife edge to allow for cutting of tissue received laterally into the first and second jaws.

6. The device of claim 1, wherein, a valley having a flat surface is between a first pair of first teeth on the first side of the first jaw and a second pair of first teeth on the first side of the first jaw.

7. The device of claim 1, wherein, when the first and second jaws are in the closed configuration, a window is defined between the serrated cutting edge of the first jaw and the serrated cutting edge of the second jaw.

8. The device of claim 1, wherein one or more first teeth of the plurality of first teeth that are positioned at the distal end of the first jaw are larger than one or more first teeth that are positioned proximate the proximal end of the first jaw, and one or more second teeth of the plurality of second teeth that are positioned at the distal end of the second jaw are larger than one or more second teeth that are positioned proximate the proximal end of the second jaw.

9. A biopsy forceps system for sampling tissue, comprising:
    a proximal assembly including an actuator;
    a tension member extending from a distal end to a proximal end coupled to the proximal assembly; and
    a distal assembly including first and second jaws movable between an open configuration, in which the jaws are separated from one another to receive target tissue therebetween, and a closed configuration, in which cutting edges of the jaws are moved toward one another to cut a portion of the target tissue from surrounding tissue, the first and second jaws defining a tissue receiving space therebetween to house the cut tissue, the first and second jaws being pivotable relative to one another, each of the jaws including a serrated cutting edge extending therealong, the distal assembly further including an attachment member extending from a distal end to a proximal end directly coupled to the tension member, the attachment member being movably coupled to the first and second jaws so that distal movement of the attachment member moves the jaws to the open configuration while proximal movement thereof moves the jaws to the closed configuration, wherein a plurality of valleys between a plurality of first teeth on a first side of the first jaw define a first line, at least two teeth of the plurality of first teeth have a first height measured from the first line, wherein the at least two teeth of the plurality of first teeth form a first valley between the at least two teeth, and at least two other teeth of the plurality of first teeth have a second height measured from the first line and different from the first height, wherein the at least two other teeth of the plurality of first teeth form a second valley between the at least two other teeth, wherein the first line intersects the first valley and the second valley at a maximum depth of each of the first valley and the second valley, wherein actuation of the proximal assembly causes the attachment member to move proximally and distally relative to the first and second jaws.

10. The system of claim 9, wherein, when the first and second jaws are in the closed configuration, a window is defined between the serrated cutting edge of the first jaw and the serrated cutting edge of the second jaw.

11. The system of claim 9, wherein each of the first jaw and the second jaw extends from a distal end to a proximal end, and wherein one or more first teeth of the plurality of first teeth that are positioned at the distal end of the first jaw are bigger than one or more first teeth that are positioned proximate the proximal end of the first jaw, and one or more second teeth of the plurality of second teeth that are positioned at the distal end of the second jaw are bigger than one or more second teeth that are positioned proximate the proximal end of the second jaw.

12. The system of claim 9, further comprising a link, comprising a proximal end and a distal end, moveably coupled to the distal end of the attachment member.

13. The system of claim 9, wherein the first jaw includes a first tooth at a distal-most end of the first jaw, the first tooth comprising a first cutting edge extending from a first valley between the first tooth and an adjacent tooth to a peak of the first tooth, a second cutting edge transverse to the first cutting edge and extending from a second valley between the first tooth and a second adjacent tooth to the peak, and a third linear cutting edge at the peak that connects the first and second cutting edges of the first tooth, and wherein the second jaw includes two second teeth that mate with the first tooth when the first jaw and the second jaw are in the closed configuration, each second tooth comprising a first cutting edge, a second cutting edge, and a third cutting edge that connects the first and second cutting edges of the respective second tooth.

14. The system of claim 9, wherein no teeth are between the two teeth having the first height, and no teeth are between the two other teeth having the second height.

15. The system of claim 14, wherein two additional teeth of the plurality of first teeth have the first height, and the two other teeth are between the two teeth having the first height and the two additional teeth.

16. The system of claim 9, wherein one of the other teeth having the second height is between the two teeth having the first height.

17. A method of obtaining a tissue sample, comprising inserting a distal portion of a biopsy forceps assembly to a target area within a body, the distal portion including:

a tension member extending from a proximal end to a distal end; and an end effector including a first jaw and a second jaw movable between an open configuration, in which the first jaw and the second jaw are separated from one another to receive target tissue therebetween, and a closed configuration, in which cutting edges of the jaws are moved toward one another to cut a portion of the target tissue from surrounding tissue, the first and second jaws defining a tissue receiving space therebetween to house the cut tissue, the first and second jaws being pivotable relative to one another, each of the jaws including a serrated cutting edge comprising a plurality of teeth extending therealong, wherein each of the first jaw and the second jaw extends from a distal end to a proximal end, and wherein one or more first teeth of the plurality of teeth that are positioned at the distal end of the first jaw are larger than one or more first teeth that are positioned proximate the proximal end of the first jaw, and one or more second teeth of the plurality of teeth that are positioned at the distal end of the second jaw are larger than one or more second teeth that are positioned proximate the proximal end of the second jaw, wherein the plurality of teeth of the first jaw further includes a first tooth, a second tooth, a third tooth, and a fourth tooth in a row, wherein a first valley is between the first tooth and the second tooth, a second valley is between the second tooth and the third tooth, and a third valley is between the third tooth and the fourth tooth, wherein a maximum depth of each of the first valley, the second valley, and the third valley defines a first line parallel to a base line extending from the distal end to the proximal end of the base of the first jaw, wherein the first tooth and the third tooth have a first height measured relative to the first line, wherein the second tooth and the fourth tooth have a second height measured relative to the first line and different than the first height, wherein the end effector further includes an attachment member extending from a distal end to a proximal end directly coupled to the tension member, the attachment member being movably coupled to the first and second jaws so that distal movement of the attachment member moves the jaws to the open configuration while proximal movement thereof moves the jaws to the closed configuration, and moving the attachment member proximally relative to the first and second jaws to pivot the jaws to the closed configuration so that the cutting edges of the first jaw and the second jaw sever the target tissue received therebetween from the surrounding tissue.

18. The method of claim 17, further comprising:
inserting the biopsy forceps assembly through a working channel of an endoscope.

* * * * *